United States Patent
Hodges et al.

(10) Patent No.: US 6,454,921 B1
(45) Date of Patent: Sep. 24, 2002

(54) ELECTROCHEMICAL CELL

(75) Inventors: Alastair M. Hodges, San Diego, CA (US); Thomas W. Beck, North Richmond; Ian A. Maxwell, Five Dock, both of (AU)

(73) Assignee: USF Filtration and Separations Group, Inc., Timonium, MD (US)

( * ) Notice: Subject to any disclaimer, the term of this patent is extended or adjusted under 35 U.S.C. 154(b) by 0 days.

(21) Appl. No.: 09/404,119

(22) Filed: Sep. 23, 1999

Related U.S. Application Data

(63) Continuation of application No. PCT/AU98/00200, filed on Mar. 25, 1998.

(30) Foreign Application Priority Data

Mar. 25, 1998 (AU) ............................................. 98/00200

(51) Int. Cl.$^7$ ............................................... G01N 27/26
(52) U.S. Cl. ........................ 204/401; 204/400; 204/403
(58) Field of Search ................ 204/400, 415, 204/403, 416, 401

(56) References Cited

U.S. PATENT DOCUMENTS

| | | | |
|---|---|---|---|
| 4,254,546 A | | 3/1981 | Ullery, Jr. |
| 4,301,412 A | | 11/1981 | Hill et al. |
| 4,301,414 A | | 11/1981 | Hill et al. |
| 4,303,887 A | | 12/1981 | Hill et al. |
| 4,591,550 A | * | 5/1986 | Hafeman et al. ........... 204/403 |
| 4,654,197 A | | 3/1987 | Lilja et al. |

(List continued on next page.)

FOREIGN PATENT DOCUMENTS

| | | |
|---|---|---|
| AU | A-54873/94 | 8/1994 |
| DE | 297 09 141 U1 | 10/1997 |
| EP | 0 170 375 B1 | 2/1986 |
| EP | 0 255 291 A1 | 2/1988 |
| EP | 0 299 779 A2 | 1/1989 |
| EP | 0 351 516 A2 | 1/1990 |
| EP | 0 351 892 A2 | 1/1990 |
| EP | 0 451 981 A2 | 10/1991 |
| EP | 0 585 933 A2 | 3/1994 |
| GB | 2 194 112 A | 2/1988 |
| JP | H5-80018 | 3/1993 |
| JP | 6-310746 | 11/1994 |
| WO | WO 89/08713 | 9/1989 |
| WO | WO 95/16198 | 6/1995 |
| WO | WO 95/28634 | 10/1995 |
| WO | WO 97/00441 | 1/1997 |

OTHER PUBLICATIONS

Derwent Abstract Accession No. 93–140898/17, class S03, JP, A., 05080018 (Rikagaku Kenkyusho) Mar. 30, 1993.
Derwent Abstract Accession No. 95–026336/04, class S03, JP, A, 06310746 (Hitachi Ltd) Nov. 4, 1944.
Patent Abstracts of Japan, JP, 9–243588 A (Matsushita Electric Ind Co. Ltd) Sep. 19, 1997.
Patent Abstracts of Japan, JP, 9–222408 A (Matsushita Electric Ind Co. Ltd) Aug. 26, 1997.
Patent Abstracts of Japan, JP, 9–236570 A (Matsushita Electric Ind Co. Ltd) Sep. 9, 1997.
International Search Report, PCT/AU 98/00200.

*Primary Examiner*—T. Tung
(74) *Attorney, Agent, or Firm*—Knobbe, Martens, Olson, and Bear, LLP

(57) ABSTRACT

The invention relates to an amperometric electrochemical cell having a first insulating substrate carrying a first electrode, a second insulting substrate carrying a second electrode, said electrodes being disposed to face each other and spaced apart by less than 500 µm, and defining a sample reservoir therebetween, and wherein at least one, and preferably both, insulating substrates and the electrode carried thereon include an electromagnetic radiation transmissive portion in registration with said reservoir. The walls of the electrochemical cell may be formed from a thin metallic portion on a transparent substrate. Such cells are useful in providing visual confirmation of the validity of the electrochemical measurement.

9 Claims, 1 Drawing Sheet

U.S. PATENT DOCUMENTS

| | | | |
|---|---|---|---|
| 4,782,265 A | | 11/1988 | Schaper et al. |
| 4,900,424 A | | 2/1990 | Birth et al. |
| 4,911,794 A | * | 3/1990 | Parce et al. .................. 204/415 |
| 4,989,452 A | * | 2/1991 | Toon et al. |
| 5,059,908 A | | 10/1991 | Mina |
| 5,120,420 A | | 6/1992 | Nankai et al. |
| 5,126,034 A | | 6/1992 | Carter et al. |
| 5,128,015 A | | 7/1992 | Szuminsky et al. |
| 5,141,868 A | | 8/1992 | Shanks et al. |
| 5,192,415 A | | 3/1993 | Yoshioka et al. |
| 5,320,732 A | | 6/1994 | Nankai et al. |
| 5,382,346 A | | 1/1995 | Uenoyama et al. |
| 5,384,028 A | | 1/1995 | Ito |
| 5,385,846 A | | 1/1995 | Kuhn et al. |
| 5,393,399 A | | 2/1995 | Van den Berg et al. |
| 5,413,690 A | | 5/1995 | Kost et al. |
| 5,437,999 A | | 8/1995 | Diebold et al. |
| 5,508,171 A | | 4/1996 | Walling et al. |
| 5,509,410 A | | 4/1996 | Hill et al. |
| 5,517,313 A | * | 5/1996 | Colvin ....................... 436/172 |
| 5,567,302 A | | 10/1996 | Song et al. |
| 5,611,908 A | | 3/1997 | Matthiessen et al. |
| 5,628,890 A | | 5/1997 | Carter et al. |
| 5,645,709 A | | 7/1997 | Birch et al. |

* cited by examiner

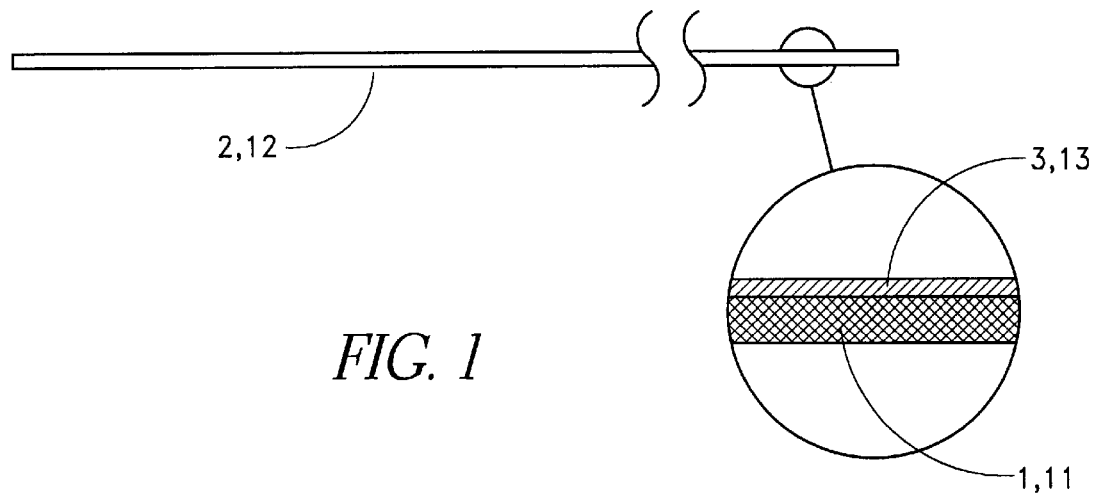
FIG. 1
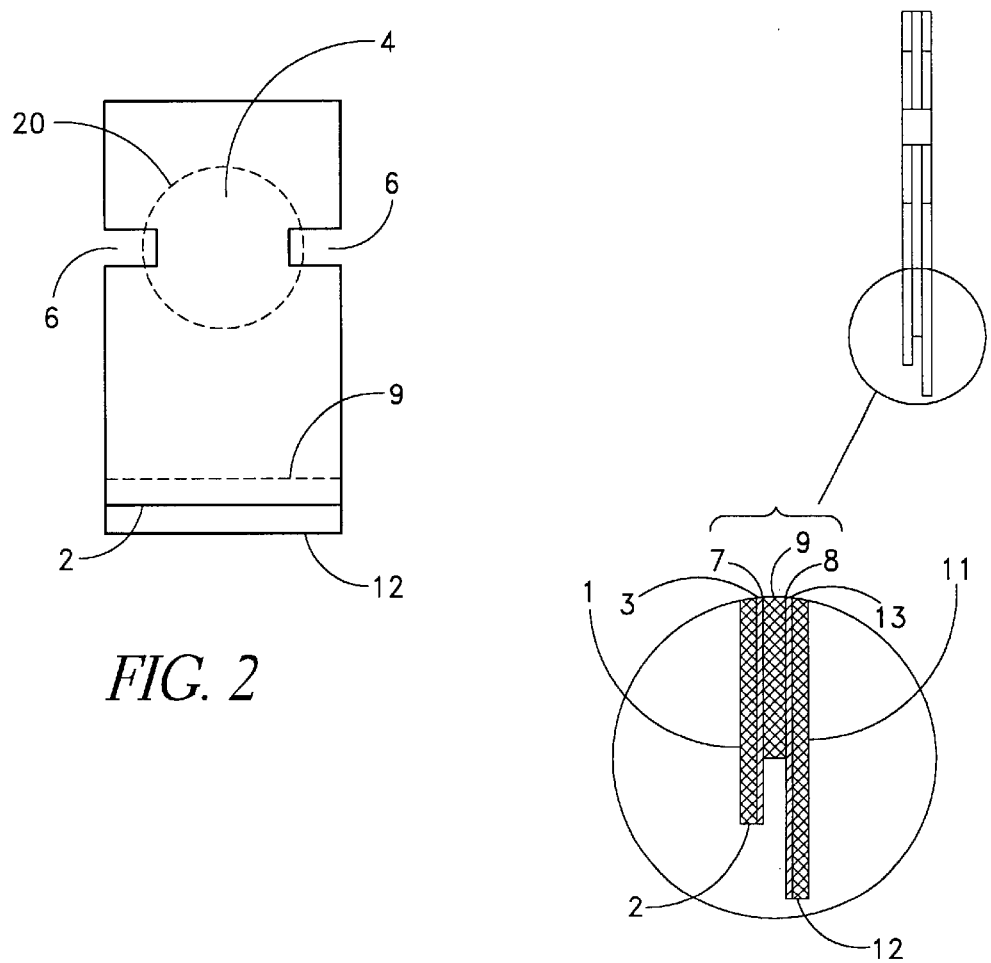
FIG. 2
FIG. 3

ELECTROCHEMICAL CELL

RELATED APPLICATIONS

This application is a continuation application of International Patent Application No. PCT/AU98/00200, internationally filed Mar. 25 1998, and claiming priority from Australian Provisional Patent Application No. PO 5857, filed Mar. 25 1997.

FIELD OF THE INVENTION

This invention relates to disposable electrochemical sensors of the type used for quantitative analysis, for example, of glucose levels in blood, or the like.

DESCRIPTION OF THE RELATED ART

Light transmissive electrodes are known in the prior art, however they have not previously been applied to amperometric cells. For example, GB 2 194 112 discloses the use of optically transparent electrodes used to drive a microelectrophoresis cell while laser Doppler velocimetry is used to determine the velocity and micro current motion of charged particles within the sample.

JP, A 05080018 discloses another approach to making transparent electrodes by the use of conductive glass for electrochromic and field emission devices.

JP, A 06310746 also teaches the use and formation of yet another type of conducting transparent electrode formed from the deposition of organic conducting polymers onto a glass slide. This type of electrode is useful in solar energy collection cells. Ullery, in U.S. Pat. No. 4,254,546 also discloses a photovoltaic cell in which the top layer is a light collecting electrode. U.S. Pat. No. 4,782,265 discloses two spaced apart translucent electrodes useful in luminescent cells. However, U.S. Pat. No. 4,782,265 specifically teaches that gold, silver, aluminum, platinum and the like are only suitable for the production of non-transmissive electrodes.

In co-pending applications PCT/AU95/00207, PCT/AU96/00365, PCT/AU96/00723 and PCT/AU96/00724 (the contents of which are incorporated herein by reference) there are described various very thin electrochemical sensors or cells. These cells include a pair of oppositely facing spaced apart electrodes which are formed as thin metal coatings (for example sputter coatings) deposited on thin inert plastic film (for example 100 micron thick PET). The electrodes are separated one from the other by a spacer of thickness of for example 500 $\mu$m or less.

Such cells may be provided with one or more fluid passageways into and out of the sample reservoir whereby the cell may be filled with an analyte and air expelled during filling. In some embodiments the analyte is drawn into the cell by the energy liberated as a reagent contained therein dissolves.

The sensors are, as discussed above, very small and normally contain only small amounts of the liquid sample. Accurate measurement requires that the cell be filled with liquid. Even minute variations in the quantity of liquid in the cell can affect the sensing measurements. It can be difficult for a user to be sure that in use the cell has been uniformly filled with a sample to be analysed.

Further, sensors of the kind under discussion are usually intended to be discarded after use. If a user is distracted after use or prior to disposal it is not always easy for the user to know which sensors have been used and which have not.

It is an object of the present invention to overcome or ameliorate at least one of the disadvantages of the prior art, or to provide a useful alternative.

SUMMARY OF THE INVENTION

According to one aspect the present invention provides an amperometric electrochemical cell comprising a first insulating substrate carrying a first electrode, a second insulating substrate carrying a second electrode, said electrodes being disposed to face each other and spaced apart by less than 500 $\mu$m, and defining a sample reservoir therebetween, wherein at least one of said insulating substrates and the electrode carried thereon includes an electromagnetic radiation transmissive portion in registration with said reservoir.

Preferably, both said insulating substrates and the electrodes thereon include a transmissive portion. Most preferably, the transmissive portion is formed by a conductive metallic coating on the substrate, which is of a thickness such that it is transparent or translucent. Suitable substances for the metallic coating include gold, indium oxide, tin oxide or mixtures thereof. A suitable substrate is PET.

According to a second aspect, the invention provides a method of filling an amperometric cell comprising the steps of:

a) drawing a liquid sample into said cell comprising a first insulating substrate carrying a first electrode, a second insulating substrate carrying a second electrode, said electrodes being disposed to face each other and spaced apart by less than 500 $\mu$m, and defining a sample reservoir therebetween, wherein at least one of said insulating substrates and the electrode carried thereon includes an electromagnetic radiation transmissive portion in registration with said reservoir b) exposing the transmissive portion to electromagnetic radiation c) monitoring a property of the electromagnetic radiation passing and/or reflected through said transmissive portion d) comparing said monitored property with a predetermined value indicative of the cell being filled, and e) continuing to draw the liquid sample into the cell until said monitored property reaches said predetermined value.

In a fifth aspect, the invention provides an apparatus for determining whether an amperometric cell according to the first aspect is filled with a liquid sample, said apparatus comprising an electromagnetic radiation means adapted to expose said transmissive portion of said cell to electromagnetic radiation, a monitoring means adapted to monitor a property of the electromagnetic radiation passing and/or reflected through said transmissive portion, and a means for determining whether said monitored property has reached a predetermined value indicative of the cell being filled.

Preferably, said apparatus may also include means to apply potential across the amperometric cell and detect the resultant current. It may also include a validation means to confirm the cell is filled with a liquid sample.

"Comprising" as herein used is used in an inclusive sense, that is to say in the sense of "including" or "containing". The term is not intended in an exclusive sense ("consisting of" or "composed of").

Light-transmissive cells intended for spectrophotometric use are well known, however this has not previously been accomplished in a cell wherein the only surfaces suitable for a window are entirely covered by a metal electrode. One skilled in the art will appreciate that whilst the embodiments of the invention are described with respect to light transmissive conductive coatings, such coatings may be also be transparent to some other forms of electromagnetic radiation which are not visible to the human eye.

BRIEF DESCRIPTION OF THE DRAWING

FIG. 1 shows a cross section of a wall of a cell according to the present invention.

FIG. 2 shows a cell according to one embodiment of the present invention.

FIG. 3 shows a cross section of the cell in FIG. 2.

DETAILED DESCRIPTION OF THE PREFERRED EMBODIMENT

An embodiment of the invention will now be described by way of example only. Referring firstly to FIG. 1, each wall of the cell, 2, 12 comprises an insulating substrate 1, 11 carrying an electrode 3, 13 thereon.

The embodiment is generally in accordance with the apparatus described in our co-pending application PCT/AU96/00724 which is incorporated herein by reference. The apparatus hereof corresponds substantially to the apparatus described in that application with the difference that electrode layer 3, 13 which in application PCT/AU96/00724 was sputter coated palladium having a thickness of 100–1000 Angstrom, is replaced according to the present invention, by a light-transmissive conductive metallic coating of a thickness such that it is transparent or translucent. Gold, indium oxide, tin oxide and mixtures of indium and tin oxides or other suitable light-transmissive conductive metallic coatings may be utilised. Those skilled in the art will appreciate that transparent inorganic and organic polymers or mixtures thereof could also be used. Substrate 1 is also light-transmissive.

In one embodiment, the cell takes the form as shown in FIGS. 2 or 3. The cell comprises a first insulating substrate 1 consisting of a Melinex® PET layer, a first electrode 3 consisting of a conductive metallic layer on substrate 1, an adhesive layer 7, a PET spacer 9, a second adhesive layer 8, a second electrode 13 formed as a metallic layer or coating on second insulating substrate 11. Spacer 9 defines a sample reservoir 4 having a thickness corresponding to the thickness of the spacer 9 together with the thickness of adhesive layers 7 and 8. Access to the sample reservoir 4 is provided at the side edge of the cell by notches 6.

At least one of the said insulating substrates and the electrode carried thereon includes an electromagnetic radiation transmissive portion 20 in registration with the reservoir 4.

In preferred embodiments of the invention, a sample to be analyzed is introduced to the cell by capillary action. The sample is placed in contact with notch 6 and is spontaneously drawn by capillary action into the reservoir 4, displaced air from the reservoir 4 venting from the opposite notch 6. A surfactant may be included in the capillary space to assist in drawing in the sample.

The cell is provided with connection means for example edge connectors whereby the cell may be placed into a measuring circuit. In a preferred embodiment this is achieved by making spacer 9 shorter than cell walls 2, 12 and by making one wall 2 of shorter length than the other 12. This forms a socket region having contact areas electrically connected with the working and counter electrodes of a sensing apparatus. A simple tongue plug having corresponding engaging conduct surfaces can then be used for electrical connection. Connectors of other form may be devised.

Chemicals for use in the cell may be supported on the cell electrodes or walls, may be supported on an independent support contained within the cell or may be self-supporting.

In use, when the cell is filled with the liquid sample, e.g. blood, a film of the sample covers the inside of the transmissive portion 20 formed by substrate 1, 11 and metal electrode 3, 13 over reservoir 4, thereby indicating to the user when the cell is adequately filled, and clearly differentiating a used sensor from an unused one.

Apart from simple visual inspection, a user can also monitor the filling of the cell by exposing the electromagnetic radiation transmissive portion 20 to electromagnetic radiation such as infra-red, ultraviolet light or laser light and monitoring a property of the electromagnetic radiation (for example, optical density, color or optical rotation) as it exits the cell, either by another transmissive portion on the opposite side of the reservoir, or as a result of internal reflection within the reservoir.

A particular embodiment of an apparatus suitable for carrying out the inventive method is hereby described. The apparatus has means for holding and orienting a cell according to the present invention and exposing the electromagnetic portion of the cell to allow an electromagnetic radiation source, e.g. a light beam, to enter the reservoir.

Optionally, the apparatus may also be equipped with means for automatically placing the cell into the said holding means.

The path of the light beam is substantially linear, and it exits the cell either via another transparent portion of the cell, or is reflected back through the first mentioned transmissive portion. The electromagnetic radiation leaving the cell is monitored by an appropriate detector. This detector monitors a property of the electromagnetic radiation leaving the cell for comparison with a predetermined value which is indicative of the cell being filled, for example if the cell is filled with blood up to or above the transmissive portion, a reduction in optical density will be detected. If the cell is empty or only partially filled to this point, the optical density will remain high but will reduce as the reservoir is filled until it reaches the predetermined value indicating a full cell. It will be appreciated that the apparatus could be made to continue filling until the cell was satisfactorily filled, by means of a feedback system. The apparatus could also be adapted so that it performed the necessary electrochemical measurements on the cell, thus reducing the need for excessive sample movement.

The apparatus preferably also includes a validation means which is triggered when it is determined that the cell is full and the sensing measurement can be accepted as valid.

As will be apparent to those skilled in the art from the teaching hereof the invention may be embodied in other forms without departing herefrom.

What is claimed is:

1. An amperometric electrochemical cell comprising a first insulating substrate carrying a first electrode, a second insulating substrate carrying a second electrode, said electrodes being disposed to face each other and spaced apart by less than 500 $\mu$m, and defining a sample reservoir therebetween, wherein at least one of said insulating substrates and the electrode carried thereon includes an electromagnetic radiation transmissive portion in registration with said reservoir, the cell further comprising a measuring circuit, an electromagnetic radiation source, and an electromagnetic radiation detector.

2. An amperometric electrochemical cell according to claim 1 wherein both of said insulating substrates and the electrodes carried thereon include a transmissive portion.

3. An amperometric electrochemical cell according to claim 1 wherein the electromagnetic radiation transmissive portion of each electrode is formed by a conductive metallic coating on said substrate(s).

4. An amperometric electrochemical cell according to claim 3 wherein the conductive metallic coating is of a thickness such that it is transparent or translucent.

5. An amperometric electrochemical cell according to claim 3 wherein the metallic coating is selected from one or more members of the group consisting of: gold, indium oxide, tin oxide and mixtures thereof.

6. An amperometric electrochemical cell according to claim 1 wherein the insulating substrate(s) is/are PET.

7. An apparatus for determining whether an amperometric cell according to claim 1 is filled with a liquid sample, said apparatus comprising means adapted to expose said transmissive portion of said cell to electromagnetic radiation from said source, said detector being adapted to monitor a property of the electromagnetic radiation passing and/or reflected through said transmissive portion; and a means for determining whether said monitored property has reached a predetermined value indicative of the cell being filled.

8. An apparatus according to claim 9 further including means to apply a potential across the amperometric cell and detect the resultant current.

9. An apparatus according to claim 7 further including a validation means to confirm that the cell is filled with liquid sample.

* * * * *